United States Patent
Levy (10) Patent No.: US 8,920,302 B2
(45) Date of Patent: Dec. 30, 2014

(54) PELVIC IMPLANT WITH ANCHORING FRAME

(75) Inventor: Gil Levy, Tel-Aviv (IL)

(73) Assignee: Prolapse Inc., Great Neck, NY (US)

( * ) Notice: Subject to any disclaimer, the term of this patent is extended or adjusted under 35 U.S.C. 154(b) by 756 days.

(21) Appl. No.: 13/160,551

(22) Filed: Jun. 15, 2011

(65) Prior Publication Data

US 2011/0245597 A1    Oct. 6, 2011

Related U.S. Application Data (63) Continuation of application No. 10/574,372, filed as application No. PCT/IL2004/001059 on Nov. 17, 2004, now Pat. No. 7,981,024.

(60) Provisional application No. 60/520,533, filed on Nov. 17, 2003.

(51) Int. Cl.
```
A61F 2/00      (2006.01)
A61B 17/42     (2006.01)
A61B 17/00     (2006.01)
```

(52) U.S. Cl.
CPC .............. *A61F 2/0063* (2013.01); *A61B 17/42* (2013.01); *A61F 2/0045* (2013.01); *A61B 2017/00805* (2013.01); *A61F 2002/0072* (2013.01)
USPC .......................................................... 600/30

(58) Field of Classification Search
CPC .................... A61B 17/42; A61B 2017/00805; A61F 2/0063; A61F 2/0045; A61F 2002/0072
USPC ........ 600/38–42, 37, 16–18, 29, 30; 606/151, 606/198, 200
See application file for complete search history.

(56) References Cited

U.S. PATENT DOCUMENTS

| | | | |
|---|---|---|---|
| 1,275,520 A | | 8/1918 | Bell |
| 2,391,343 A | | 12/1945 | Popper |
| 3,422,817 A | | 1/1969 | Mishkin et al. |
| 5,334,217 A | | 8/1994 | Das |
| 5,366,460 A | | 11/1994 | Eberbach |
| 5,433,727 A | | 7/1995 | Sideris |
| 5,578,045 A | | 11/1996 | Das |
| 5,634,931 A | * | 6/1997 | Kugel ........................... 606/151 |

(Continued)

FOREIGN PATENT DOCUMENTS

| | | |
|---|---|---|
| WO | WO 96/32882 | 10/1996 |
| WO | WO 99/07289 | 2/1999 |

(Continued)

OTHER PUBLICATIONS

Response Dated Nov. 28, 2011 to Communication Pursuant to Article 94(3) EPC of May 31, 2011 From the European Patent Office Re.: Application No. 04799366.2.
International Preliminary Report on Patentability Dated Jun. 1, 2006 From the International Bureau of WIPO Re.: Application No. PCT/IL2004/001059.
International Search Report and the Written Opinion Dated Jul. 25, 2005 From the International Searching Authority Re.: Application No. PCT/IL04/01059.

(Continued)

*Primary Examiner* — Samuel Gilbert (57) ABSTRACT

An implant for a pelvis is provided, wherein suturing is not necessary for anchoring the implant in place. The implant includes a flexible sheet and a solid frame, wherein the frame can be compressed or expanded. Upon insertion through the narrow openings of the pelvis, the frame is compressed, and upon delivery at the site, the frame is expanded, and is designed to anchor to the surrounding anatomical structures.

16 Claims, 5 Drawing Sheets

(56) References Cited

U.S. PATENT DOCUMENTS

| | | | |
|---|---|---|---|
| 5,656,012 | A | 8/1997 | Sienkiewicz |
| 5,709,707 | A | 1/1998 | Lock et al. |
| 5,824,082 | A * | 10/1998 | Brown ............... 623/11.11 |
| 5,879,366 | A | 3/1999 | Shaw et al. |
| 5,904,703 | A | 5/1999 | Gilson |
| 6,174,320 | B1 * | 1/2001 | Kugel et al. ............ 606/151 |
| 6,176,863 | B1 * | 1/2001 | Kugel et al. ............ 606/151 |
| 6,189,535 | B1 | 2/2001 | Enhorning |
| 6,197,036 | B1 * | 3/2001 | Tripp et al. ............ 606/151 |
| 6,592,515 | B2 | 7/2003 | Thierfelder et al. |
| 6,645,137 | B2 | 11/2003 | Ulmsten et al. |
| 6,656,206 | B2 | 12/2003 | Corcoran et al. |
| 6,755,781 | B2 | 6/2004 | Gellman |
| 6,786,861 | B1 | 9/2004 | Pretorius |
| 7,981,024 | B2 * | 7/2011 | Levy .................... 600/37 |
| 2002/0068950 | A1 | 6/2002 | Corcoran et al. |
| 2007/0088189 | A1 | 4/2007 | Levy |

FOREIGN PATENT DOCUMENTS

| | | |
|---|---|---|
| WO | WO 00/27304 | 3/2000 |
| WO | WO 01/17435 | 3/2001 |
| WO | WO 2005/046511 | 5/2005 |

OTHER PUBLICATIONS

Communication Pursuant to Article 94(3) EPC Dated Feb. 5, 2010 From the European Patent Office Re.: Application No. 04799366.2.

Communication Pursuant to Article 94(3) EPC Dated May 31, 2010 From the European Patent Office Re.: Application No. 04799366.2.

Examiner's Report Dated Nov. 19, 2009 From the Australian Government, IP Australia Re.: Application No. 2004288660.

Notice of Allowance Dated Mar. 11, 2011 From the US Patent and Trademark Office Re. U.S. Appl. No. 10/574,372.

Official Action Dated Sep. 9, 2010 From the U.S. Patent and Trademark Office Re. U.S. Appl. No. 10/574,372.

Response Dated Aug. 1, 2010 to Communication Pursuant to Article 94(3) EPC of Feb. 5, 2010 From the European Patent Office Re.: Application No. 04799366.2.

Response Dated Dec. 21, 2010 to Official Action of Sep. 9, 2010 From the US Patent and Trademark Office Re. U.S. Appl. No. 10/574,372.

Supplementary European Search Report Dated Oct. 24, 2008 From the European Patent Office Re.: Application No. 04799366.2.

Communication Under Rule 71(3) EPC Dated Mar. 19, 2013 From the European Patent Office Re.: Application No. 04799366.2.

* cited by examiner

PELVIC IMPLANT WITH ANCHORING FRAME

RELATED APPLICATIONS

This application is a continuation of U.S. patent application Ser. No. 10/574,372 filed Dec. 1, 2006, which is a National Phase of PCT Patent Application No. PCT/IL2004/001059 having International filing date of Nov. 17, 2004, which claims the benefit of priority of U.S. Provisional Patent Application No. 60/520,533 filed Nov. 17, 2003. The contents of the above applications are all incorporated herein by reference.

FIELD AND BACKGROUND OF THE INVENTION

The present invention relates to an implant for the pelvis and, more particularly, to an implant which can be held in place without suturing.

Pelvic floor disorders include cystocele, rectocele, enterocele and uterine and vaginal prolapse. These disorders are often a consequence of weakness or damage to pelvic muscles and ligaments, caused by childbearing, hysterectomy, connective tissue defects, atrophy, or physical injury. Two basic approaches to remedying this condition have been the use of a removable device known as a pessary, or surgery to replace or repair parts of the pelvic supporting structures.

A pessary is a vaginal insert, having a specified geometric configuration such as, for example, a cube or a donut, which can be temporarily placed in the vaginal canal. Examples of such devices are disclosed in U.S. Pat. No. 6,645,137; U.S. Pat. No. 6,189,535, and many others.

The surgical approach includes reconstruction of the damaged support tissue using sutures or replacement of the support tissue with an implant or device. An example of such a device is disclosed in U.S. Pat. No. 6,786,861 to Pretorius. The device disclosed therein is a sling having a flexible elongate member and a distensible portion, and is configured to be inserted dorsally between the urethra and pelvic bone, with ends of the elongate member attachable to retropubic or ischial structures. Another such device is disclosed in U.S. Pat. No. 6,755,781 to Gellman. The device disclosed therein is a medical sling having one or more cuts are disposed in the material. The cuts on the sling provide open areas to permit tissue ingrowth and crosslinking when the sling is implanted inside the body of the patient. These types of slings and supporting devices are configured to treat urinary incontinence rather than prolapse, and as such, they are generally located under the urethra or bladder neck.

Other devices for implantation within a pelvis are described. U.S. Pat. No. 6,592,515 to Thierfelder, for example, discloses an implant useful for a sacral colpopexy procedure for treating vaginal prolapse. The implant includes tissue engagement portions, which are configured for anchoring the implant into bone. World Publication WO 00/27304 to Ory et al. discloses a suspension device for treating prolapse and urinary incontinence, including a suspension cord, non-absorbable material, and anchoring parts which are designed to be fixed by suturing or stapling means to implanting walls.

All of these devices require suturing to anchor the device to the anatomical structures within the pelvis. This leads to difficulties and potential complications, as sharp needles must be placed deep within the pelvis into an area which is difficult to access. Furthermore, the stability of these implants depends on the strength of the suture, a material which can sometimes tear, and on the strength of the supporting ligaments, which may also be weak due to disease, old age, or wear from childbirth. The sutures are inflexible, and cannot accommodate dynamic pressures from the abdomen above. Finally, the use of sutures requires sharp corners or edges on the implant material, which are not suited to the contoured shape of the anatomy of the pelvis.

There is thus a widely recognized need for, and it would be highly advantageous to have, a surgical implant devoid of the above limitations.

SUMMARY OF THE INVENTION

According to one aspect of the invention there is provided a device for implantation in a pelvis. The device includes a sheet having a perimeter and a frame for holding the sheet at a portion of the perimeter, wherein the frame includes a first arm, a second arm, and a connecting element connecting the first arm and the second arm.

According to another aspect of the invention, there is provided a device for treating prolapse of a pelvic organ. The device includes a flexible sheet and a frame in contact with the sheet, the frame having a first configuration in which the frame is compressed, thereby causing the sheet to be configured in a compressed position, and the frame having a second configuration in which the frame is expanded, thereby allowing the sheet to be configured in an expanded position.

According to another aspect of the invention, there is provided a sutureless implantable device for supporting a pelvic organ, the device having contoured edges.

According to further features in preferred embodiments of the invention described below, the sheet includes a first layer and a second layer, and the frame is positioned between the first and second layers. The sheet generally has a substantially flat configuration, and is a mesh, a sheath, a diaphragm or a divider and may be comprised of biological material.

According to yet further features in preferred embodiments of the invention, the frame comprises biodegradable, flexible material. The connecting element can include a pivot or a ratchet, and may be an angled member. Alternatively, the connecting element comprises an elastic material. In preferred embodiments, the device also includes an adjusting element for controlling a proximity of the first arm of the frame to the second arm. The adjusting element can be a wire, a ratcheting device or a pulley wire.

According to yet another aspect of the invention, there is provided a method for treating prolapse of a pelvic organ. The method includes providing a device having a sheet, and a frame in contact with the sheet, the frame having a first configuration in which the frame is compressed and having a second configuration in which the frame is expanded, compressing the frame into the first configuration, introducing the device through a vagina, inserting the device into a space between the vagina and the pelvic organ, and expanding the frame into the second configuration, wherein the expanding includes anchoring the frame into an anatomical structure.

According to further features in preferred embodiments of the invention described below, the compressing and expanding can include pulling a wire, ratcheting, or bending a portion of the frame. The inserting can include inserting the device into a space between the vagina and a bladder, or between the vagina and a rectum.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a pelvic implant which can be used to temporarily or permanently support the organs of a pelvis. Specifically, the present invention can be used to prevent or treat vaginal prolapse, prolapse of the bladder (Cystocele), prolapse of the uterus, prolapse of the rectum (Rectocele), or any other herniation of organs through the pelvic floor.

The principles and operation of a device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1-4 are illustrations of an implant device 10 for insertion into a pelvis, in accordance with various embodiments of the invention. Device 10 includes a frame 12 and a sheet 14. For the purposes of the present application, the term "sheet" can be understood to include, but not be limited to, a mesh, sheath, diaphragm, divider or multi-layered sheet. Frame 12 is an anchoring system for anchoring sheet 14 into place in the pelvis. Frame 12 is designed to be adjustable, such that upon insertion into the pelvis, device 10 is compressible to a satisfactory size for introduction through the passageway leading into the pelvis, and such that once device 10 is situated within the pelvis, device 10 is expandable to a size at which frame 12 can anchor device 10 in place.

Figure 1A:
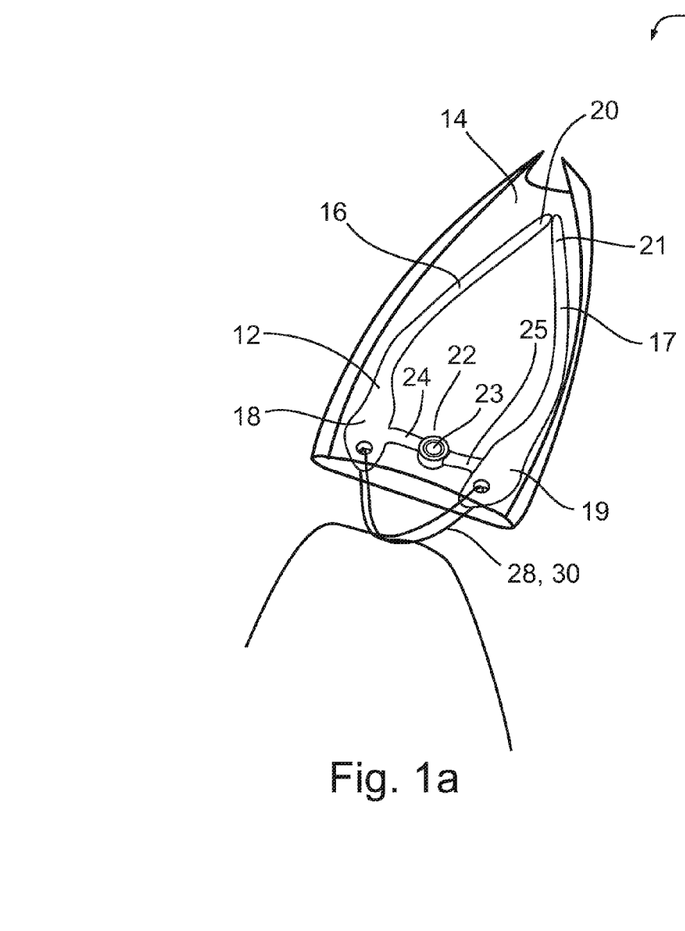
FIGS. 1a and 1b are illustrations of an implant in accordance with one embodiment of the present invention, shown in its compressed and expanded states, respectively.
Figure 1B:
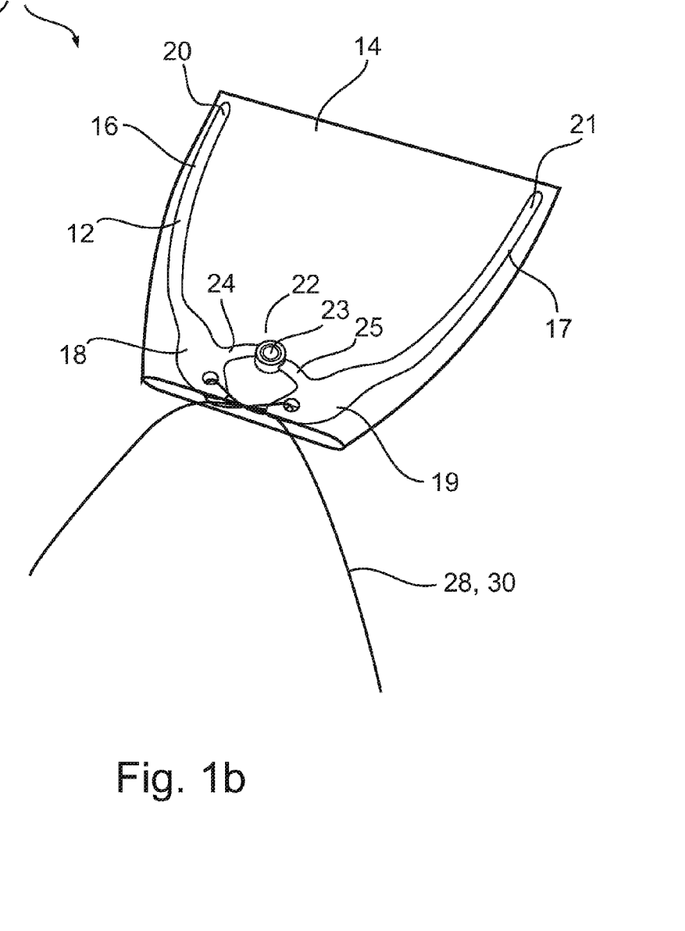

Reference is now made to FIGS. 1a and 1b, which are illustrations of device 10 in a compressed configuration and an expanded configuration, respectively, in accordance with a first embodiment of the present invention. Frame 12 includes two arms 16, 17 each of which has a proximal end 18, 19 and a distal end 20, 21. The two arms 16 and 17 are connected to one another at proximal ends 18 and 19 by a connecting element 22. Connecting element 22 has at least two configurations, such that in a first configuration, proximal ends 18 and 19 of arms 16 and 17 are together, as shown in FIG. 1a, and in a second configuration, proximal ends 18 and 19 of arms 16 and 17 are apart, as shown in FIG. 1b. In the embodiment shown in FIGS. 1a and 1b, connecting element 22 includes two connectors 24, 25 and a pivot 23. Pivot 23 allows connectors 24, 25 to bend with respect to one another, thereby allowing for multiple configurations of connecting element 22. Connecting element 22 can be positioned in its open or closed configuration by the use of an adjusting element 28. In the embodiment shown in FIGS. 2a and 2b, adjusting element 28 is a fastener 30, for holding proximal ends 18 and 19 together. Fastener 30 can be a wire (as shown), a ratchet, or any other mechanical means suitable for pulling and holding proximal ends 18 and 19 together. Specifically, in the embodiment shown, a wire is attached to proximal ends 18 and 19 of arms 16 and 17. By pulling on a portion of the wire, connecting element 22 changes configuration and proximal ends 18 and 19 are joined together. This leads to a moving apart of distal ends 20 and 21, thereby causing an expansion of frame 12.

Figures 2A, 2B, 2C:
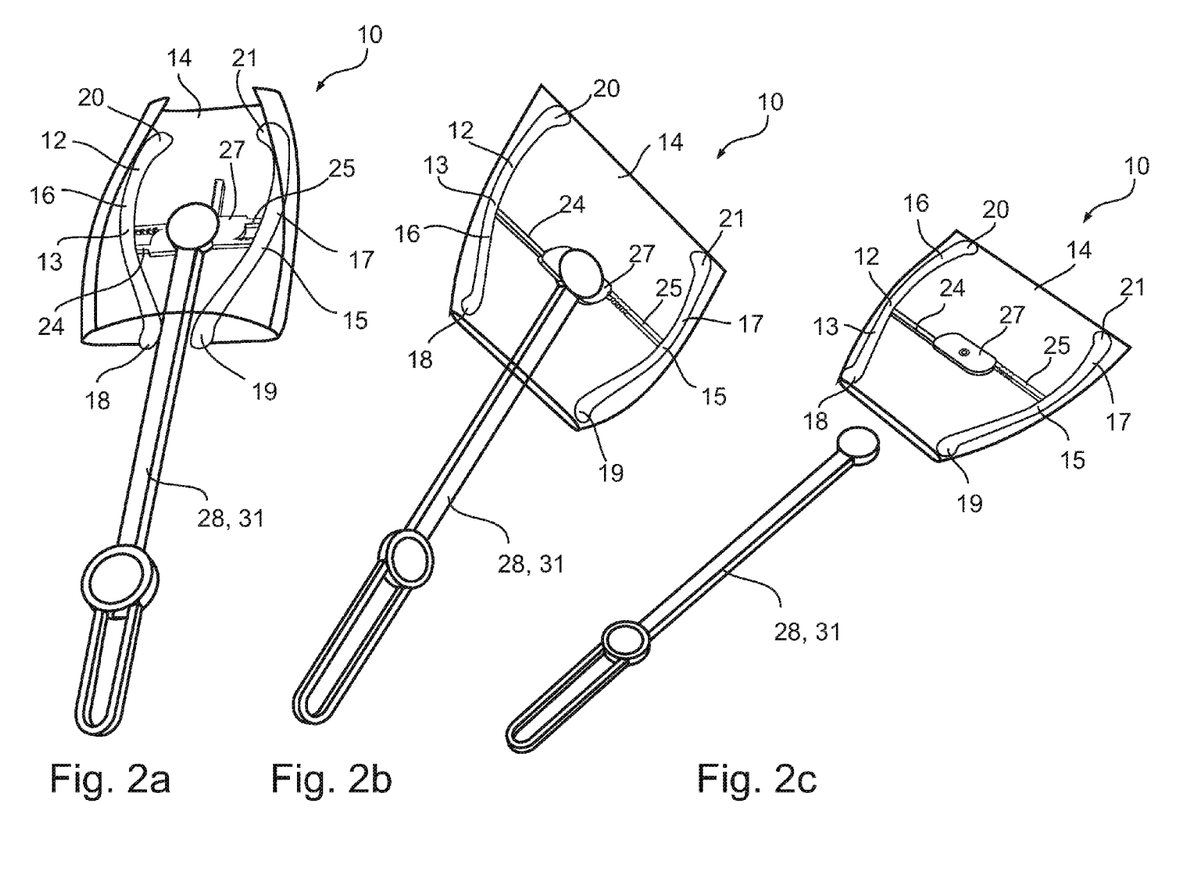
FIGS. 2a-c are illustrations of an implant in accordance with another embodiment of the present invention, shown in its compressed, expanded and delivered states.

Reference is now made to FIGS. 2a-2c, which are illustrations of device 10 in a compressed configuration and expanded configurations, in accordance with another embodiment of the present invention. Frame 12 includes two arms 16, 17 each of which has a proximal end 18, 19, a distal end 20, 21, and a body 13, 15 between said proximal and distal ends. The two arms 16 and 17 are connected to one another somewhere along the length of body 13, 15, preferably at a mid-point thereof, by a connecting element 22. Connecting element 22 has at least two configurations, such that in a first configuration, arms 16 and 17 are close together, as shown in FIG. 2a, and in a second configuration, arms 16 and 17 are relatively far from one another, as shown in FIGS. 2b and 2c. In the embodiment shown in FIGS. 2a and 2b, connecting element 22 includes two connectors 24, 25 and a ratchet 27. Ratchet 27 allows connectors 24, 25 to move together or apart from one another, thereby allowing for multiple configurations of connecting element 22. Connecting element 22 can be positioned in its open or closed configuration by the use of an adjusting element 28. In the embodiment shown in FIGS. 2a-2c, adjusting element 28 is a separate ratcheting device 31, for bringing arms 16 and 17 together or pushing them apart. During introduction of device 10 into the pelvis, connecting element 22 is configured such that arms 16 and 17 are close together, a shown in FIG. 2a. When the desired location within the pelvis is reached, connecting device is configured such that arms 16 and 17 are apart, thereby causing an expansion of frame 12 as shown in FIG.

2b. When expansion of frame 12 is complete, ratcheting device 31 can be removed, leaving device 10 in place in the body.

Figure 3A:
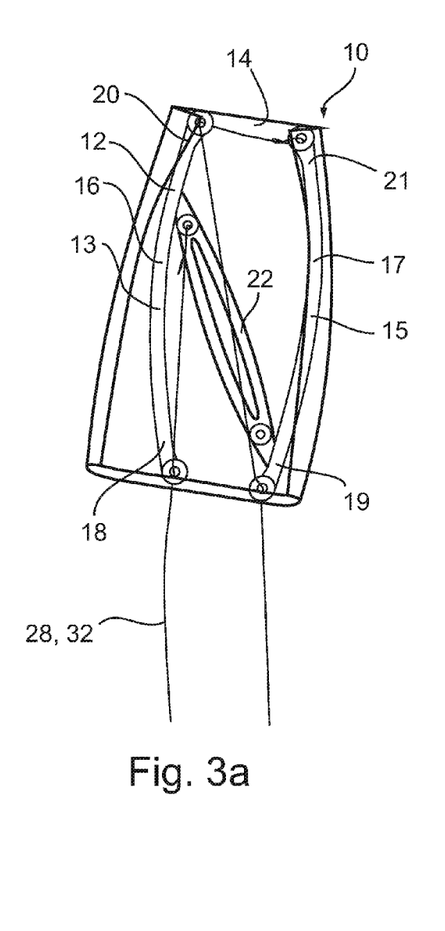
FIGS. 3a and 3b are illustrations of an implant in accordance with yet another embodiment of the present invention, shown in its compressed and expanded states, respectively.
Figure 3B:
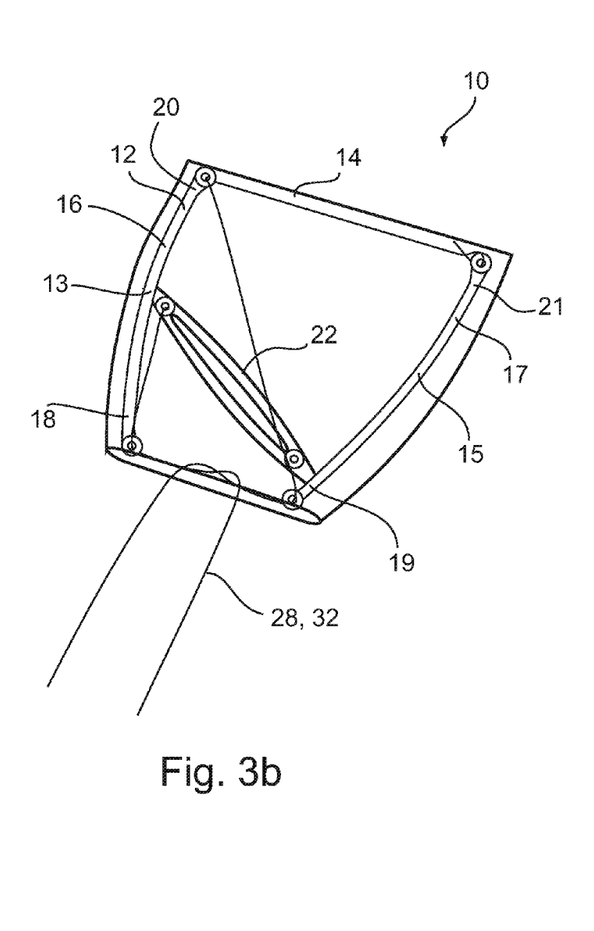

Reference is now made to FIGS. 3a and 3b, which are illustrations of device 10 in a compressed configuration and an expanded configuration, respectively, in accordance with yet another embodiment of the present invention. Frame 12 includes two arms 16, 17 each of which has a proximal end 18, 19 and a distal end 20, 21 and a body 13, 15. The two arms 16 and 17 are connected to one another at a point along bodies 13, 15 by a connecting element 22. Connecting element 22 has at least two configurations, such that in a first configuration, arms 16 and 17 are close together, as shown in FIG. 3a, and in a second configuration, arms 16 and 17 are relatively far from one another, as shown in FIG. 3b. In the embodiment shown and described herein with respect to FIGS. 3a and 3b, connecting element 22 is an angled member, configured at an angle with respect to arms 16 and 17 and set up as a pulley system with a wire. Pulling on the wire causes connecting element 22 to be pulled down at one end, changing the angle between connecting element 22 and arms 16 and 17, causing arms 16 and 17 to be pushed apart from one another. Connecting element 22 can be positioned in its open or closed configuration by the use of an adjusting element 28. In the embodiment shown in FIGS. 3a and 3b, adjusting element 28 is a pulley wire 32, for holding proximal ends 18 and 19 together. Specifically, in the embodiment shown, pulley wire 32 is connected to both arms 16 and 17 and connecting element 22. By pulling on a portion of pulley wire 32, the angle between connecting element 22 and arms 16 and 17 changes, leading to a moving apart of arms 16 and 17.

Figure 4A:
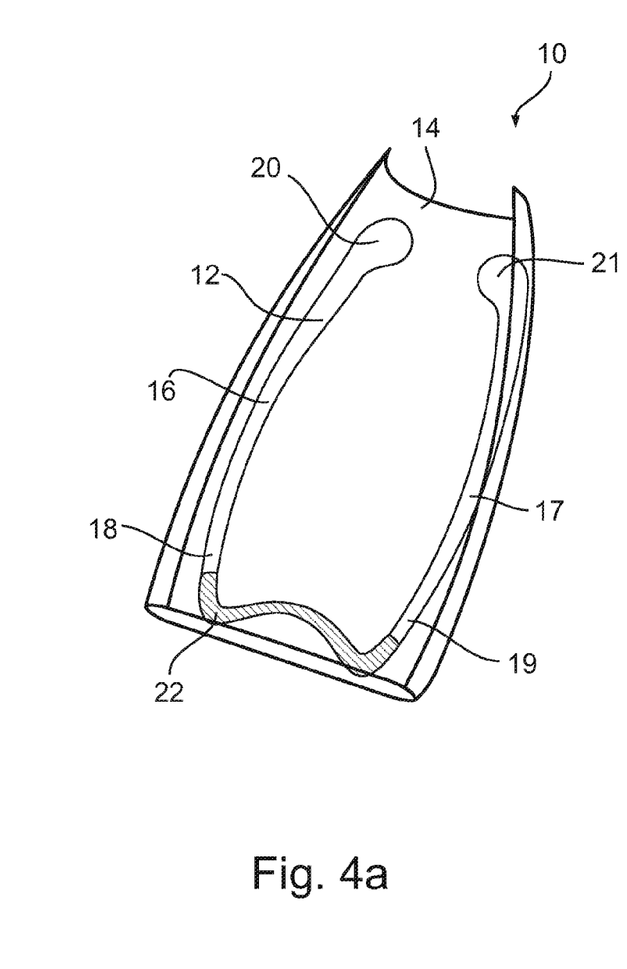
FIGS. 4a and 4b are illustrations of an implant in accordance with yet another embodiment of the present invention, shown in its compressed and expanded states, respectively.
Figure 4B:
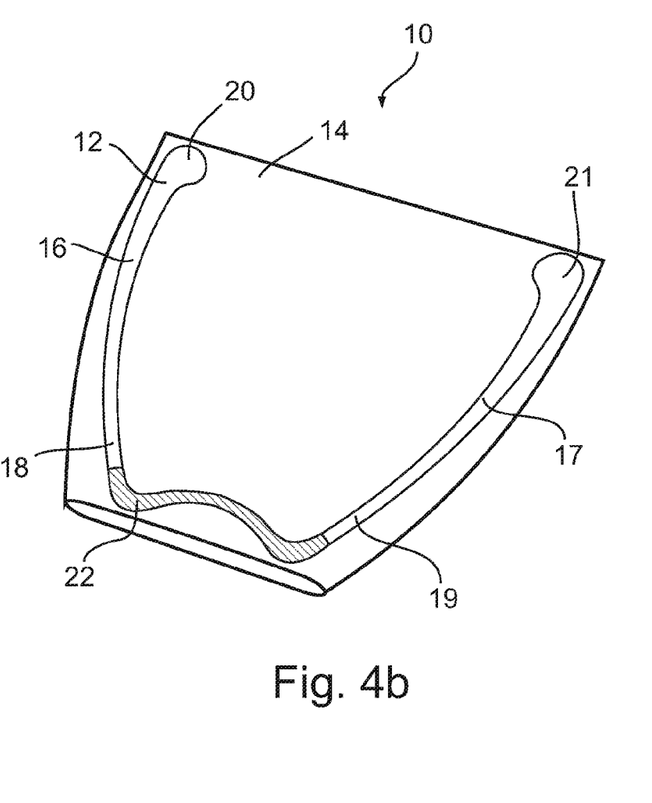

Reference is now made to FIGS. 4a and 4b, which are illustrations of device 10 in a compressed configuration and an expanded configuration, respectively, in accordance with a most preferred embodiment of the present invention. Frame 12 includes two arms 16, 17 each of which has a proximal end 18, 19 and a distal end 20, 21. The two arms 16 and 17 are connected to one another at proximal ends 18 and 19 by a connecting element 22. Connecting element 22 is a flexible, elastic band, capable of compressing or expanding. In a first configuration, arms 16 and 17 are relatively close together, as shown in FIG. 4a, and in a second configuration, arms 16 and 17 are apart, as shown in FIG. 4b. In this embodiment, no separate adjusting element 28 is necessary.

Sheet 14 is a flexible member, comprised of a nylon mesh, a biological material (such as animal tissue, for example), or any other flexible biocompatible material. For example, sheet 14 may be comprised of Prolene™, nylon, polypropylene, Deklene™, polylactic acid, polyethylene glycol, polyester, synthetic biomaterials, allografts, autologous tissue, xenografts, heterografts, or any combination of the above, or any other biocompatible material which is flexible and suitable for supporting a pelvic organ. In a preferred embodiment, sheet 14 includes two layers, so that frame 12 can fit into the space between the two layers, without the need separate connectors for connecting the frame 12 to the sheet 14. In a preferred embodiment, both layers of sheet 14 are comprised of the same material. In an alternative embodiment, a combination of materials is used. Frame 12 is comprised of a solid, supportive material, such as a polymer, a metal, or any other biocompatible material. For example, frame 12 may be comprised of polylactic acid, polyethylene glycol, synthetic biomaterials, titanium, stainless steel, shape-memory alloys, or any combination of the above, or any other biocompatible material which is flexible and suitable for providing support to sheet 14. In a preferred embodiment, frame 12 is comprised of a biodegradable material so that over time, frame 12 will degrade and be replaced by scar tissue which can then act as a support for sheet 14.

Figure 5:
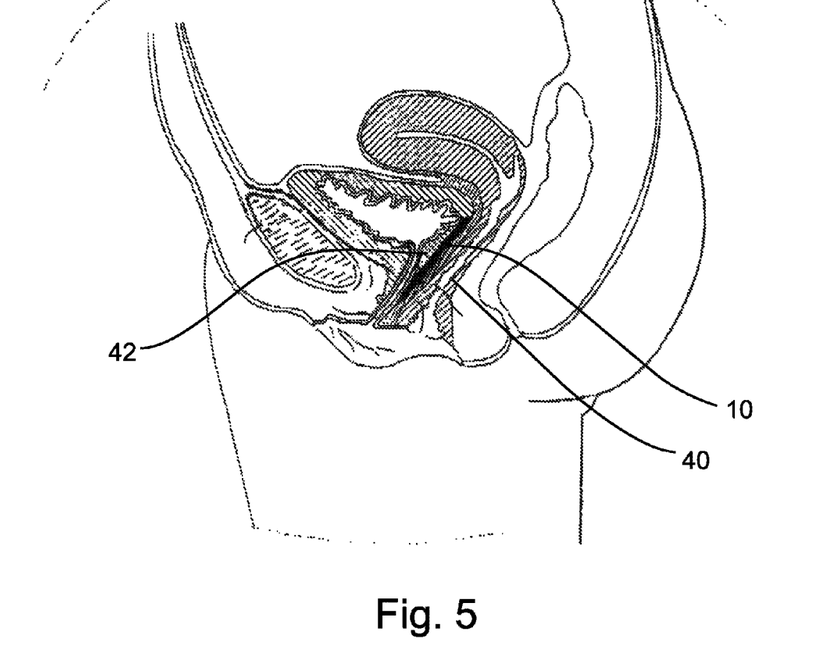
FIG. 5 is a cross sectional illustration of the implant of FIGS. 1-4, implanted between the vagina and bladder.

A method for treating bladder prolapse is described with reference to FIGS. 5 and 6. A patient is set up for surgery, placed in a gynecological position, and anesthetized. A weighted speculum is placed in the lower vaginal wall to expose the prolapsed upper vaginal wall. An incision is made along the center of the upper wall of the vagina 40. In a preferred embodiment, the incision is approximately 1 mm deep and 4 cm long. Using a sharp instrument such as a scissor, the vagina 40 is separated from the bladder wall through the initial incision. Alternatively, the vagina is separated from the bladder wall 42 using blunt dissection—such as with the tip of a finger. These types of incisions and separations are well-known in the art, and the methods of the present invention are not limited to the details included herein. Device 10 is compressed and inserted through the vagina and situated between the vagina and the bladder. Device 10 is then expanded into its expanded position, wherein arms 16 and 17 are situated against the pelvic sidewalls 44 in gentle tension holding it in place. The vaginal incision is then sutured closed under the implanted device 10. As shown in FIG. 5, device 10 is situated between the vagina and the bladder, supporting the bladder and preventing it from descending into the vaginal canal.

Figure 6:
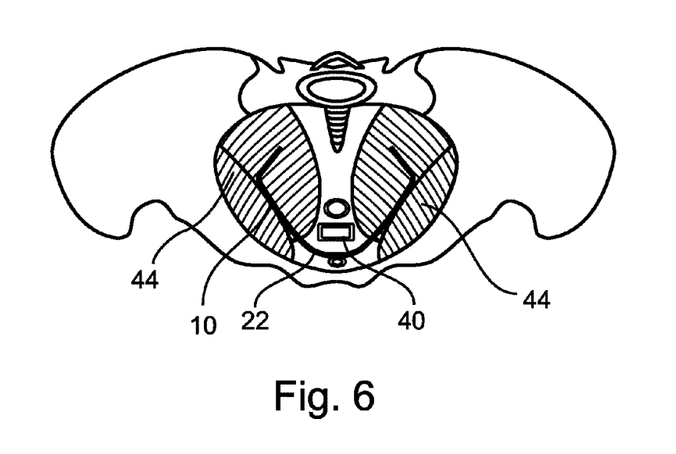
FIG. 6 is an upper view of the delivered implant in position between the vagina and bladder.

In a preferred embodiment, connecting element 22 is in an anterior portion of device 10 upon insertion, as shown in FIG. 6. In an alternative embodiment, connecting element 22 is in a posterior portion of device 10 upon insertion.

In an alternative embodiment, an incision is made between the vagina and the bladder, and device 10 is inserted into a position that provides support of the bladder, with the frame compressed against the para-rectal compartment. In this embodiment, device 10 would be similar in shape, but generally smaller in size than device 10 used for bladder support.

Device 10 can include several different sizes for different sized patients.

In alternative embodiments, device 10 or portions thereof may be coated or incorporated with therapeutic materials.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:
1. A vaginal support comprising:
a sheet having a perimeter; and
a frame configured for holding said sheet at a portion of said perimeter, wherein said frame comprises:

a first arm unattached to a frame element at a first end and connected at a second end to a connecting element;

a second arm unattached to a frame element at a first end and connected at a second end to the connecting element; and the connecting element, comprising an elastic material, connecting said first arm and said second arm, wherein the vaginal support is sized and shaped for insertion through a vaginal wall of a patient and for expansion against pelvic side walls so as to thereby support organs of a pelvis without suturing.

2. The vaginal support of claim 1, wherein the vaginal support has a substantially trapezoidal configuration, with a distal base narrower than a proximal base.

3. The vaginal support of claim 1, wherein said sheet comprises a first layer and a second layer.

4. The vaginal support of claim 1, wherein the sheet is comprised of a material selected from the group consisting of Prolene™, nylon, Deklene™T, polylactic acid, polyethylene glycol, polyester, and synthetic biomaterials.

5. The vaginal support of claim 1, wherein said sheet is selected from the group consisting of a sheath, a diaphragm and a divider.

6. An implantable device for pelvic floor repair, comprising:

a flexible mesh sheet having a perimeter; and a support frame configured for holding said sheet at a portion of said perimeter, and configured for expanding said sheet into a substantially flat configuration, including expanding the device against a pelvic wall without suturing, wherein said support frame comprises:

a first arm unattached to a frame element at one end and connected at one end to a connecting element;

a second arm unattached to a frame element at one end and connected at one end to the connecting element; and the connecting element, comprising an elastic material, connecting said first arm and said second arm.

7. The implantable device of claim 6, in which said frame has a first configuration in which said frame is compressed, thereby causing said sheet to be configured in a compressed position, and said frame has a second configuration in which said frame is expanded, thereby allowing said sheet to be configured in an expanded position.

8. The implantable device of claim 6, wherein said expanding comprises unbending said frame.

9. The implantable device of claim 6, in which said frame is comprised of at least one of a group consisting of polylactic acid, polyethylene glycol, synthetic biomaterials and stainless steel.

10. The implantable device of claim 6, in which said frame is comprised of shape-memory alloy.

11. A method for supporting herniation of an organ through the pelvic floor comprising:

inserting a supporting device via an incision in a vaginal wall, while said supporting device is in a compressed configuration;

allowing said supporting device to expand against pelvic sidewalls into a substantially flat configuration after passing through said vaginal wall, wherein the supporting device comprises:

a sheet having a perimeter; and an expanding frame comprising an elastic connecting element attached to one end of each of two arms and another end of each of the two arms being unattached to a frame element, configured for holding said sheet at a portion of said perimeter; and suturing the vaginal wall.

12. The method of claim 11 in which the suturing the vaginal wall is performed without suturing the supporting device.

13. The method of claim 11, wherein the supporting device, upon expansion, treats vaginal prolapse.

14. The method of claim 11, wherein the supporting device, upon expansion, treats prolapse of the bladder.

15. The method of claim 11, wherein the supporting device, upon expansion, treats prolapse of the uterus.

16. The method of claim 11, wherein the supporting device, upon expansion, treats prolapse of the rectum.

* * * * *